United States Patent [19]

Kablaoui et al.

[11] 4,028,258
[45] June 7, 1977

[54] ALKYLENE OXIDE ADDUCTS OF PHOSPHOSULFURIZED N-(HYDROXYALKYL) ALKENYLSUCCINIMIDES

[75] Inventors: Mahmoud S. Kablaoui, Wappingers Falls, N.Y.; Robert E. Reid, Houston; Arthur W. Godfrey, Sugarland, both of Tex.

[73] Assignee: Texaco Inc., New York, N.Y.

[22] Filed: Dec. 3, 1975

[21] Appl. No.: 636,906

[52] U.S. Cl. .............................. 252/46.7; 252/78.5; 260/326.5 A; 260/326.5 S; 260/326.5 F
[51] Int. Cl.² .......................................... C10M 1/48
[58] Field of Search ............................ 252/46.7, 78; 260/326.5 A, 326.5 S, 326.5 F

[56] References Cited

UNITED STATES PATENTS

| | | | |
|---|---|---|---|
| 3,185,646 | 5/1965 | Anderson et al. | 252/46.7 |
| 3,185,647 | 5/1965 | Anderson et al. | 252/46.7 |
| 3,235,497 | 2/1966 | Lee | 252/46.7 |
| 3,342,735 | 9/1967 | Reed et al. | 252/46.7 |
| 3,359,347 | 12/1967 | Cyba | 252/46.7 X |
| 3,513,093 | 5/1970 | Le Suer | 252/46.7 X |
| 3,623,985 | 11/1971 | Hendrickson | 252/46.7 X |
| 3,756,951 | 9/1973 | Dickert | 252/46.7 |
| 3,954,798 | 5/1976 | Romine | 252/46.7 X |

Primary Examiner—Delbert E. Gantz
Assistant Examiner—Andrew H. Metz
Attorney, Agent, or Firm—Thomas H. Whaley; Carl G. Ries; Robert A. Kulason

[57] ABSTRACT

An alkylene oxide adduct of phosphosulfurized N-(hydroxyalkyl) alkenylsuccinimide characterized by the formula:

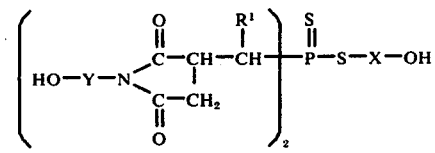

where $R^1$ is alkenyl of from 10 to 30 carbons and X and Y are divalent saturated aliphatic hydrocarbon radicals of from 2 to 6 carbons. In addition, automatic transmission fluid compositions and concentrates thereof comprising a major amount of a lubricating oil and a friction modifying amount of the alkylene oxide adduct and method of operating an automatic transmission having friction sensitive power transmitting means employing the aforedescribed automatic transmission fluid composition.

15 Claims, No Drawings

ALKYLENE OXIDE ADDUCTS OF PHOSPHOSULFURIZED N-(HYDROXYALKYL) ALKENYLSUCCINIMIDES

BACKGROUND OF INVENTION

The demand for improved performance of automatic transmission fluids spurs a continuing search for new additives and lubricating oil formulations to achieve the desired goals. An automatic transmission is a complex hydraulic mechanism having friction sensitive power transmitting means which incorporates the function of a torque converter, wet clutches and planetary gearing in a relatively compact scale unit. The device requires a transmission fluid which provides lubricity, extreme pressure, dispersant and antiwear properties as well as carefully selected frictional properties. In addition, the fluid must not be corrosive to copper alloys or any way deleterious to the synthetic seals and transmission. Another requirement for the fluid is that it maintain good lubricity and friction modifying properties under prolonged high shear, high temperature conditions encountered in this environment.

Carboxylic acids and their derivatives are widely employed as lubricity agents or friction modifiers in mineral base automatic transmission fluids. These lubricity agents provide commercial automatic transmission fluids having good service life. However, the industry is continually searching for friction modifying additives which have improved stability properties and antiwear properties and thereby increase the operational life of the automatic transmission fluid. A breakdown in stability of the friction modifier is indicated by rising coefficient of friction in the transmission fluid and by an early onset of erratic harsh shifting in service and in automatic transmission tests.

One such improved automatic transmission fluid of superior stability is described in U.S. Pat. No. 3,879,306 having improved friction modifier stability which contain as a friction modifier N-(hydroxyalkyl) alkenyl succinamic acide characterized by the formula:

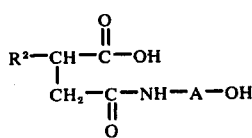

or a mixture of said succinamic acid and N-(hydroxyalkyl) alkenylsuccinimide characterized by the formula:

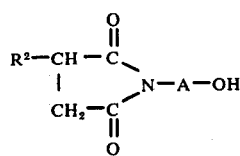

where $R^2$ is alkenyl of from 10 to 30 carbons and A is a divalent saturated aliphatic hydrocarbon radical of from 1 to 6 carbons.

SUMMARY OF INVENTION

We have discovered and this constitutes our invention a novel friction modifier product of improved stability for automatic transmission and automatic transmission fluid containing same. Specifically, the novel transmission fluid including the concentrate thereof comprises at least about 50 wt. % of a mineral oil of lubricating viscosity and between about 0.01 and 50 wt. % of the novel alkylene oxide adduct of a phosphosulfurized N-(hydroxyalkkyl) alkenyl succinimide characterized by the formula:

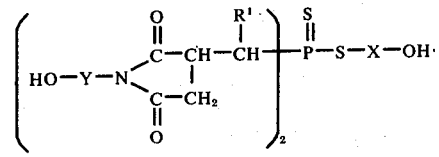

where $R^1$ is alkenyl of from 10 to 30 carbons and X and Y are divalent saturated aliphatic hydrocarbon radicals of from 2 to 6 carbons. We have further discovered a novel method of invention comprising operating an automatic transmission having friction sensitive power transmitting means by supplying to the mechanism the above described transmission fluid.

DETAILED DESCRIPTION OF THE INVENTION

As heretofore stated, the automatic transmission fluid of the invention and concentrates thereof comprise at least 50 wt. % of a hydrocarbon oil of lubricating viscosity and from about 0.01 to about 50 wt. % of the novel alkylene oxide adduct. The automatic transmission fluid concentrate contemplated herein will normally comprise between about 50 and 85 wt. % of mineral base oil and between about 5 and 50 wt. % of the alkylene oxide adduct friction modifier. In the finished formulations which are normally prepared by dilution of the concentrates with additional mineral oil the lubricating base comprises at least about 85% of the formulation and the friction modifier represents between about 0.01 and 5 wt. % of the formulation the remainder of the finished formulation containing one or more additional additives normally found in automatic transmissions. The concentrate is the form normally employed for shipment and/or storage of the product and is diluted to the finished form for use.

The novel alkylene oxide friction modifier adduct can be prepared by reacting an alkene of from 10 to 30 carbons with maleic anhydride approximately on an equal mole basis generally at a temperature between about 75° and 100° C., preferably in an inert atmosphere using an inert liquid solvent, if necessary, to render the mixture fluid for a period normally between about 2 and 10 hours to form an alkenyl succinic anhydride characterized by the formula:

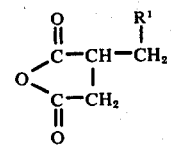

where $R^1$ is as heretofore defined.

As a next step the formed alkenyl succinic anhydride is reacted with phosphorus pentasulfide at a temperature between about 100° and 180° C. utilizing a mole ratio of anhydride to pentasulfide of between about 1:1 and 4:1, preferably in an inert atmosphere and utilizing an inert liquid solvent, for a period of normally between about 1 and 3 hours to form the phosphosulfurized derivatives characterized by the formula:

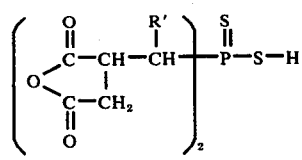

where $R^1$ is as heretofore defined.

As a third step the phosphorus pentasulfide derivative is heated, preferably in an inert gas atmosphere, to a temperature of between about 100° and 150° C. and alkylene oxide of from 2 to 6 carbons is then introduced therein utilizing a mole ratio of alkylene oxide to pentasulfide derivative of between about 1:0.5 and 1:1 to form the alkylene oxide adduct of the phosphorus pentasulfide derivative characterized by the formula:

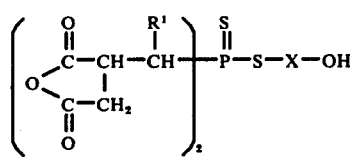

where $R^1$ and X are as heretofore defined.

As a final step the alkylene oxide derivative is contacted with alkanolamine characterized by the formula of $HO-Y-NH_2$ where Y is a divalent saturated aliphatic hydrocarbon radical of from 2 to 6 carbons at a temperature between 50° and 100° C. utilizing a mole ratio of alkanolamine to alkylene oxide derivative of between about 2:1 for a period of between about 0.5 and 1.5 hours, desirably in an inert atmosphere, to form the alkylene oxide adduct of phosphosulfurized N-(hydroxyalkyl)-n-alkenylsuccinimide characterized by the formula:

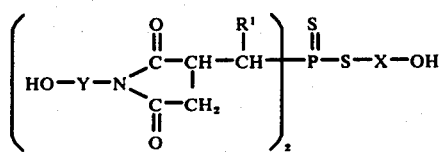

where $R^1$, X and Y are as heretofore defined.

In the foregoing four step method of preparation inert liquid diluent is normally employed in amounts of between about 30 and 70 wt. % of the reaction mixture in order to facilitate reactant contact, particularly when one or more of the reactants are solids. The liquid diluent is usually a mineral lubricating oil which also forms part of the concentrate or finished products or organic solvent such as volatile organic solvents.

Examples of suitable alkene reactants are decene, dodecene, tetradecene, octadecene and tricosene. Examples of the alkylene oxide reactants are alkylene oxide, propylene oxide, 2,3-butylene oxide, 1,2-butylene oxide, 3,4-hexylene oxide and 2,3-hexylene oxide.

Examples of the alkanolamine reactants are monoethanolamine, 1,2-propanolamine, 1,3-propanolamine, 1,2-butanolamine, 1,3-butanolamine and 2,3-pentanolamine.

Suitable inert solvents are benzene, toluene, xylene, isooctane, heptane and mixtures thereof.

The inert gas normally employed is nitrogen.

Examples of the alkylene oxide adduct products contemplated herein are as follows:

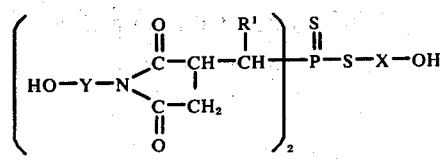

where $R^1$ is undecenyl, X and Y are $-CH_2-CH_2$; where $R^1$ is octadecenyl, X is

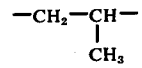

and Y is $-CH_2-CH_2-CH_2-$; where $R^1$ is tetracosenyl, X is $-CH_2-CH_2-CH_2-CH_2-CH_2-$ and Y is

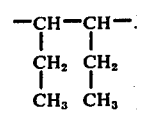

The finished automatic transmission fluid of the invention will generally be a formulated fluid containing minor amounts of the conventional additives. For example, the automatic transmission fluid can contain in addition to the contemplated friction modifiers between about 0.5 and 5 wt. % of an ashless dispersant such as the succinimide reaction product of a polyalkylene polyamine and $C_{50}{}^+$ alkenyl succinic anhydride, between about 0.5 to 8 wt. % of mixed alkyl esters of methacrylic acid having molecular weights about 25,000 as VI improvers; between about 0.1 to 5 wt. % of a zinc dialkyl or diaryl dithiophosphate as a wear inhibitor; between about 0.1 and 5 wt. % alkyl or aryl substituted phenyl or naphthyl amine as corrosion inhibitor; 0.1 to 5 wt. % of a bis alkyldithiothiadiazole as an antioxidant; and between about 0.1 and 5 wt. % alkali metal alkyl or alkaryl sulfonate as demulsifier. The aforementioned conventional additives are listed as merely typical. Equivalent additives thereof are also contemplated.

The automatic transmission fluid of the invention is generally characterized by an SUS viscosity at 210° F. of between about 49 to 60, a viscosity index of at least about 150 and pour point below −40° F. and meets the essential Dexron specification set by General Motors for automatic transmission fluids.

The mineral lubricating oil base which constitutes at least 85 wt. % of the finished composition and at least 50 wt. % of the concentrate composition is a refined oil or a mixture of refined oils selected according to the viscosity requirements of the particular service. For automatic transmissions where the requirements include an SUS viscosity of the compounded oil at 210° F. of 49 minimum up to 60 and at 0° F. of 7000 maximum (extrapolated) the base oil or the major component thereof is generally a distilled oil lighter than an SAE 10 Motor Oil, such as one having an SUS viscosity at 100° F. less than 150 and generally between 50 and 125. Example distillate fractions are paraffinic distillate or combinations of paraffinic/naphthenic distillates. The flash point of the distillate component of the base oil will generally be substantially above 300° F., if the distillate fraction constitutes the entire base oil, its flash point will usually be above 350° F.

A particularly preferred base oil comprises approximately 70 to 95 wt. % of a refined distillate oil and 5 to 30 wt. % of a refined residual fraction which imparts desired high flash point and lubricity to the base oil. A specifically preferred residual fraction comprises a paraffin base residuum which has been propane deasphalted and subjected to centrifuge dewaxing having an SUS viscosity at 210° F. below about 250. An effective base oil mixture comprises 85 wt. % of a furfural refined, acid treated, clay contacted, solvent dewaxed paraffin base distillate having an SUS viscosity at 100° F. and a pour point about +10° F., and 15 wt. % of an acid treated naphthenic base distillate having an SUS at 100° F. of 60, a flash above 300° F., a pour point below 40° F.

A viscosity index improvement of the formulated finished automatic transmission fluid of the invention is normally effected with a methacrylate ester polymer having the formula:

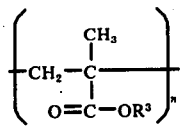

where $R^3$ is an alkyl group, a dialkylaminoalkyl group, or a mixture of such groups containing from 1 to 20 carbons and $n$ is an integer providing a molecular weight of the polymer in the range of 25,000 to 1,250,000 and preferably 35,000 to 200,000. Methacrylate ester polymers possessing pour depressant and viscosity index improving properties are well known, e.g., U.S. Pat. No. 2,737,496. Very effective material of this type is a copolymer of the lower $C_4$-$C_{14}$ alkyl methacrylate esters and the higher $C_{15}$ to $C_{20}$ alkyl methacrylate esters. A commercial methacrylate copolymer of this type which is primarily a viscosity index improver corresponds to the formula in which $R^3$ represents about 32 wt. % lauryl, 28 wt. % butyl and 26 wt. % stearyl and 14 wt. % hexyl. It is understood that other types of VI improvers can be employed. The polymethacrylates are also employed to depress pour point.

As heretofore stated, a dispersant, preferably an ashless dispersant is generally present in the finished automatic transmission fluid. One such effective dispersant is the alkenyl succinimides characterized by the general formula:

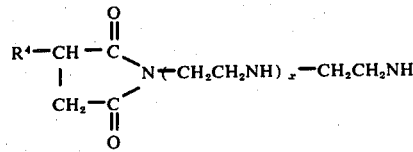

where $R^4$ is a large substantially monoolefinic aliphatic hydrocarbon radical of from 60 to 200 carbons and $x$ is an integer of from 1 to 10. Particularly suitable derivatives are the diethylene triamine, triethylene tetramine, tetraethylene pentamine of polyisobutylene succinic anhydride, particularly where $R^4$ is between about 700 and 2000, e.g., about 1300 molecular weight. These ashless dispersants are further described in U.S. Pat. Nos. 3,172,892 and 3,202,678.

Antioxidants are usually found in the fully formulated automatic transmission fluids. Effective antioxidants are the aryl substituted amine antioxidants exemplified by phenyl naphthyl amines, see U.S. Pat. No. 3,414,618 as well as compounds such as phenylenediamine, phenothiazine, diphenylamine. Particularly preferred antioxidants are phenyl-alphanaphthylamine and a mixture of 2,2'-diethyl-4,4'-dioctylphenylamine and 2,2'-diethyl-4-t-octyldiphenylamine. These antioxidants further function as corrosion inhibitors in the finished transmission fluid. Other suitable antioxidants which also function as antiwear agents are the bis alkyl dithiothiadiazole such as a 2,5-bis-octyl dithiothiadiazole.

Other valuable components contemplated in the finished compositions are the hydrocarbyl dithiophosphates which function principally as corrosion inhibitors, antiwear and antioxidants. Particularly effective compounds in this class are the zinc di(nonylphenoxyethyl)-dithiophosphate, zinc di(dodecylphenoxyethyl) dithiophosphate, zinc di(nonylphenyl)dithiophosphate, zinc dioctyldithiophosphate, zinc dihexyldithiophosphate and zinc di-(nonylphenoxyethyl) dithiophosphate. In a typical preparation zinc di(nonylphenoxyethyl) dithiophosphate is prepared by reacting p-nonylphenoxyethanol with phosphorus pentasulfide followed by neutralization of the acid formed with a basic zinc compound, such as zinc carbonate, zinc oxide or zinc hydroxide. The general preparation and description of the compounds in this class is disclosed in U.S. Pat. Nos. 2,344,395 and 3,293,181. In use it is convenient to prepare a mineral oil solution of the zinc di($C_6$-$C_{16}$ alkylphenoxypolyoxyalkyl) dithiophosphate containing from between about 50 to 75 wt. % of the zinc salt. These salt not only function as corrosion inhibitors but act as oxidation inhibitors as well, particularly when employed in concentrations of between about 0.1 and 5 wt. % of the automatic transmission fluid composition.

Still other components contemplated are ashless antiwear agents to replace zinc dithiophosphates and demulsifiers such as the sodium alkyl or aryl sulfonates.

Antifoaming agents are conventionally employed in the automaic transmission fluids because the fluids are rapidly circulated in operation and air can be entrapped. For this purpose a silicone fluid of high viscosity such as dimethyl silicone polymer having a kinematic viscosity at 25° C. of about 1000 centistokes and above is preferably employed. A very satisfactory antifoam agent for this purpose is prepared by diluting 10 grams of dimethyl silicone polymer (1000 centistokes at 25° C.) with kerosene to provide a solution of 100 cs. From about 0.005 to 0.025 percent by weight of this concentrate is generally employed in the hydraulic fluid to provide from about 50 to 200 ppm of the silicone polymer based on the transmission fluid composition.

The following examples further illustrate the invention but are not to be construed as limitations thereof.

EXAMPLE I

This example illustrates a method of preparing alkenyl succinic anhydride intermediate.

Tetradecene-1 (1176 grams, 6 moles) and maleic anhydride (558 grams, 6 moles) in a 3 liter flask were heated to reflux under nitrogen (179° C.) over a period of 4 hours during which the temperature was brought up to 230° C. The reaction mixture was kept at 230° C. for ¾ hour. The solution was cooled and unreacted starting material distilled at 130°-160° C. (25-50 mm Hg). The residue obtained weighed 1643 grams and was identified by infrared, nuclear magnetic resonance, iodine number, Saponification No. and molecular weight to be tetradecenyl succinic anhydride in an amount of about 90 wt. % and amount of 10 wt. % of an impurity of polymeric material.

EXAMPLE II

This example illustrates the conversion of the tetradecenyl succinic anhydride intermediate prepared in Example I into the alkylene oxide friction modifier adduct.

To 240 grams (0.8 mole) of n-tetradecenyl succinic anhydride in 500 mls. of xylene and 310 grams of naphthenic oil of an SUS viscosity at 100° F. of about 100 there was slowly added 88 grams (0.4 mole) of phosphorus pentasulfide. The above mixture was then heated to reflux (140° C.) under a nitrogen blanket for about 1.5 hours until all the phosphorus pentasulfide had reacted. The reaction mixture was then cooled and filtered.

The filtrate was charged to a flask equipped with a stirrer, thermometer, nitrogen inlet, dry ice condenser and ethylene oxide inlet tube. The solution was heated under nitrogen to 125° C. and the nitrogen was disconnected and ethylene oxide was bubbled therethrough to maintain the above temperature. A total of 38 grams (0.8 mole) of ethylene oxide were introduced. The reaction was then cooled to 20° to 30° C. and 49 grams (0.8 mole) of monoethanolamine was added dropwise maintaining a temperature of the solution of 50° to 65° C. The solution was heated to 110° C. under nitrogen for 1 hour, cooled and then filtered. The xylene was stripped under vacuum to give 606 grams (equivalent 90% yield) of the ethylene oxide adduct of phosphosulfurized N-(2-hydroxyethyl)-n-tetradecylsuccinimide characterized by the formula:

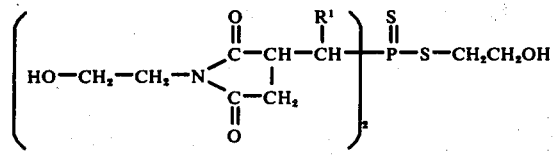

where $R^1$ is tridecenyl.

The analysis of the above product found the following:

| Analysis | Observed, wt. % | Calculated, wt.% |
|---|---|---|
| Nitrogen | 1.7 | 2.0 |
| Phosphorus | 2.2 | 2.3 |
| Sulfur | 6.7 | 4.7 |

EXAMPLE III

The procedure of Example II was repeated except n-dodecenyl succinic anhydride is used instead of n-tetradecenyl succinic anhydride. Analysis of the final product determined it to be the ethylene oxide adduct of phosphosulfurized N-(2-hydroxyethyl)n-dodecenylsuccinimide characterized by the formula:

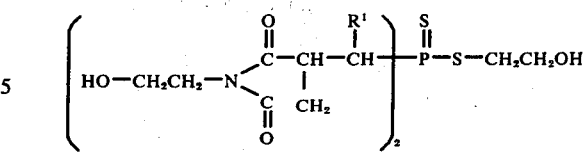

where $R^1$ is undecenyl.

Analysis of the final product gave the following:

| Analysis | Observed, Wt. % | Calculated, Wt. % |
|---|---|---|
| Nitrogen | 1.9 | 2.2 |
| Phosphorus | 2.3 | 2.3 |
| Sulfur | 6.5 | 4.8 |

EXAMPLE IV

This example illustrates the finished automatic transmission fluid compositions contemplated herein and further demonstrates their superiority in respect to friction modifier stability.

The friction stable property of the automatic transmission compositions of the invention and comparative compositions was determined in the Dexron T-12 Test. A description of the test is as follows:

DEXRON T-12 TEST

The Dexron T-12 Test with minor variation is described in the General Motors Dexron Automatic Transmission Fluid Specification issued April, 1967. This test is conducted using a Chevrolet engine with its corresponding Powerglide transmission mounted on a test stand in such a manner that the power output is absorbed by a Dynamatic 1519 eddy current dynamometer and an auxiliary inertia wheel increasing total system inertia to 17.54 lb.ft./sec.$^2$. The automatic transmission fluid is maintained at a temperature of about 275° F. The fluid must have a test life of at least 225 hours to pass this qualifying test. Test life of 400 or more hours represents premium friction qualifying properties.

The transmission fluid under test is used to fill the Powerglide transmission and is tested by running the engine and transmission in a continuous series of 90 second cycles each consisting of four phases as follows: acceleration for 13.8 seconds open throttle power with upshift occurring at approximately 12-13 seconds after start, deceleration for 8.3 seconds power off (closed throttle) coast down in the top gear (no downshift), acceleration for 9.0 seconds power on (immediate force to kickdown to low) followed by upshift approximately 9 seconds after start, and deceleration for 58.3 second power off. This sequence is continued until shift failure (excessive clutch slippage, upshift time over 0.9 second or abnormal shift).

The quality of shifting is determined as follows: at the time of upshift, the actual shifting is normally smoothly accomplished in about 0.4 seconds. After a period of essentially uniform shift time and smooth operation, the shifting becomes erratic or the shifting period begins to approach 0.8 to 0.9 seconds. The qualify to shifting is then markedly deteriorated and the duration of smooth shifting has ended. The determination of shift smoothness is made both through its audible effect and by measurement at occasional interviews of torque changes with single cycles as clutch engagement proceeds.

The fully formulated formulations reprentative of the invention and comparative formulations together with their test results are set forth below in Table I:

TABLE I

TRANSMISSION FLUID COMPOSITION AND TESTING

| Composition, Wt. % | A | B | C |
| --- | --- | --- | --- |
| Mineral Oil (~100 SUS at 100° F.) | 90.0 | 90.7 | 91.4 |
| Diethyl-t-(mono & di) octyldiphenylamine | 0.6 | 0.6 | 0.6 |
| Zinc Dialkylphenyldithiophosphate | 0.8 | 0.8 | 0.8 |
| Polyisobutylene (~1200 m.w. succinimide of tetraethylene pentamine | 2.2 | 1.0 | 1.0 |
| Tetrapolymer of butyl, lauryl, stearyl and dimethylaminoethyl methacrylate in oil (40 wt. % Polymer) | 6.0 | 6.0 | 6.0 |
| Sodium Sulfonate in oil (80 wt. % Sulfonate) | — | 0.5 | — |
| Bis-Octyl Dithiothiadiazole | — | 0.2 | — |
| Silicone Antifoam, PPM | 150 | 150 | 150 |
| Red Dye, PPM | 128 | 128 | 128 |
| Friction Modifier | | | |
| *Ethylene Oxide Product | 0.4 | — | — |
| N-Oleoylsarcosine | — | 0.2 | — |
| N-(2-Hydroxyethyl)n-tetradecenyl succinimide | — | — | 0.2 |
| Tests | | | |
| Dexron T-12, Hrs, to Fail | 429 | 293 | 300 |

*50 wt. % Product of Example II in mineral oil (100 SUS at 100° F.)

As can be seen from the table, representative composition A is substantially superior to comparative Compositions B and C in respect to friction modifier stability as measured by the number of hours of failure in the Dexron T-12. It is to be noted both friction modifiers utilized in comparative Compositions B and C are known effective friction modifiers.

We claim:

1. An alkylene oxide adduct of a phosphosulfurized N-(hydroxyalkyl) alkenyl succinimide characterized by the formula:

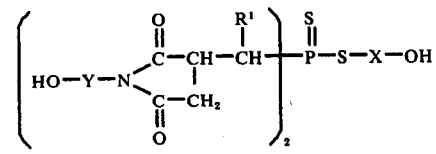

where R¹ is alkenyl of from 10 to 30 carbons and X and Y are divalent saturated hydrocarbon radicals of from 2 to 6 carbons.

2. A product in accordance with claim 1 wherein R¹ is tridecenyl and X and Y are —CH₂CH₂—.

3. A product in accordance with claim 1 wherein R¹ is undecenyl and X and Y are —CH₂CH₂—.

4. A product in accordance with claim 1 wherein R¹ is tridecenyl, X is —CH₂CH₂— and Y is —CH₂CH₂CH₂—.

5. A product in accordance with claim 1 wherein R¹ is tridecenyl, X is —CH₂CH₂— and Y is

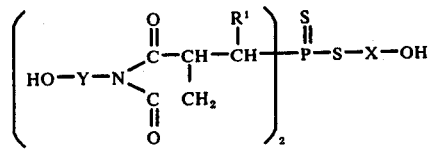

6. An automatic transmission fluid composition comprising at least about 50 wt. % of a mineral lubricating oil and between about 0.01 and 50 wt. % of an alkylene oxide adduct of phosphosulfurized (N-hydroxyalkyl)-alkenylsuccinimide characterized by the formula:

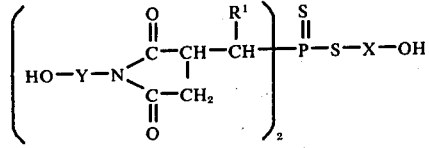

where R¹ is alkenyl of from 10 to 30 carbons and X and Y are divalent saturated aliphatic hydrocarbon radicals of from 2 to 6 carbons.

7. A composition in accordance with claim 6 wherein R¹ is tridecenyl and X and Y are —CH₂CH₂—.

8. A composition in accordance with claim 6 wherein R¹ is tridecenyl, X is —CH₂CH₂—.

9. A composition in accordance with claim 6 wherein R¹ is tridecenyl, X is —CH₂CH₂— and Y is —CH₂CH₂CH₂—.

10. A composition in accordance with claim 6 wherein R¹ is tridecenyl, X is —CH₂CH₂— and Y is

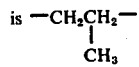

11. A method for operating an automatic transmission which comprises supplying to said transmission a fully formulated lubricating oil composition comprising at least about 85 wt. % of a mineral lubricating oil and between about 0.01 and 5 wt. % of an alkylene oxide adduct of phosphosulfurized N-(hydroxyalkyl) alkenyl succinimide characterized by the formula:

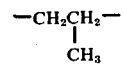

where R¹ is alkenyl of from 10 to 30 carbons and X and Y are divalent saturated aliphatic hydrocarbon radicals of from 2 to 6 carbons.

12. A method in accordance with claim 11 wherein R¹ is tridecenyl and X and Y are —CH₂CH₂—.

13. A method in accordance with claim 11 wherein R¹ is undecenyl and X and Y are —CH₂CH₂—.

14. A method in accordance with claim 11 wherein R¹ is tridecenyl, X is —CH₂CH₂— and Y is —CH₂CH₂CH₂—.

15. A method in accordance with claim 11 wherein R¹ is tridecenyl, X is —CH₂CH₂— and Y is

* * * * *